United States Patent [19]

Muller

[11] Patent Number: 5,022,414

[45] Date of Patent: Jun. 11, 1991

[54] TISSUE SEPARATOR METHOD

[75] Inventor: George H. Muller, Ann Arbor, Mich.

[73] Assignees: Joseph J. Berke, Detroit, ; a part interest; A.I.R. Foundation, Ann Arbor; Detroit Neurosurgical Foundation, Detroit, all of Mich.

[21] Appl. No.: 874,445

[22] Filed: Jun. 16, 1986

Related U.S. Application Data

[63] Continuation-in-part of Ser. No. 582,971, Nov. 21, 1983, Pat. No. 4,709,697, which is a continuation of Ser. No. 214,006, Dec. 9, 1980, abandoned, which is a continuation-in-part of Ser. No. 103,206, Dec. 13, 1979, Pat. No. 4,357,940.

[51] Int. Cl.$^5$ .............................................. A61B 17/00
[52] U.S. Cl. ...................................... 128/898; 606/190
[58] Field of Search ................... 128/304, 305, 305.1, 128/310, 755, 24 A, 20, 303 R, 898; 604/22; 15/405, 316 R; 222/3; 239/DIG. 21, DIG. 20, DIG. 22; 30/123.3; 606/190

[56] References Cited

U.S. PATENT DOCUMENTS

| | | | |
|---|---|---|---|
| 742,305 | 10/1903 | Garhart | 128/303 R |
| 3,828,771 | 8/1974 | Gartner | 128/62 A |
| 4,019,260 | 4/1977 | Levy et al. | 34/97 |
| 4,106,501 | 8/1978 | Ozbey | 128/62 A |
| 4,294,251 | 10/1981 | Greenwald et al. | 128/240 |
| 4,357,940 | 11/1982 | Muller | 606/190 |
| 4,411,265 | 10/1983 | Eichenlaub | 128/304 X |

FOREIGN PATENT DOCUMENTS

| | | | |
|---|---|---|---|
| 448013 | 7/1975 | U.S.S.R. | 128/305 |
| 301032 | 1/1930 | United Kingdom | 30/123.3 |

Primary Examiner—Michael H. Thaler

[57] ABSTRACT

A method of and structure for separating tissue. The method comprises the step of directing a fluid medium under pressure from a tissue separator including a floating tip at the tissue while floating the tip of the separator on the fluid medium. The tissue may be living tissue and in accordance with the method of the invention may be separated along natural cleavage planes. The fluid medium may be a gas or liquid and may be regulated in pressure and formed in pulses. It may be passed around and/or through the floating tip. The tissue to be separated may also be nudged by the floating tip. The fluid medium may be treated water from a municipal water supply or separate container and may be passed over a high surface to fluid interacting soap-like, replaceable cartridge made of at least one of an abrading, cleansing, polishing, and geriocidal material within the tissue separator structure prior to being directed at the tissue to be separated. The tissue separator, in addition to including a floating tip and means for performing the above method steps, may also include means for suctioning from the area of the tissue being or to be separated.

24 Claims, 7 Drawing Sheets

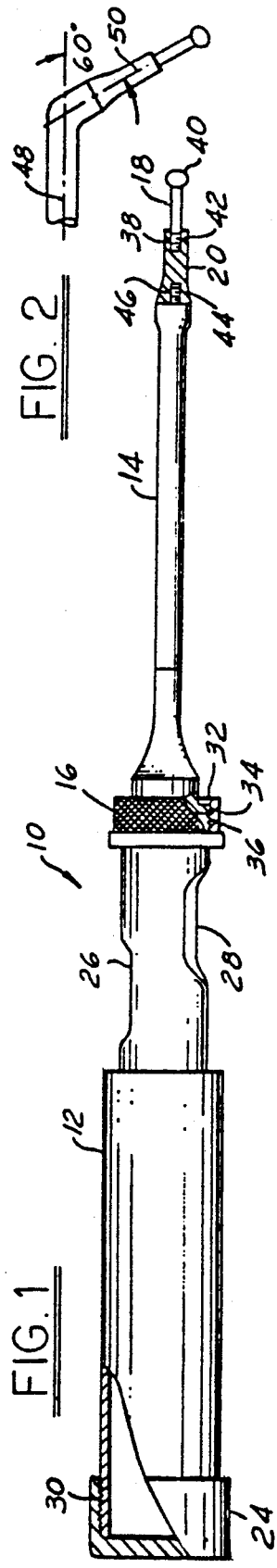
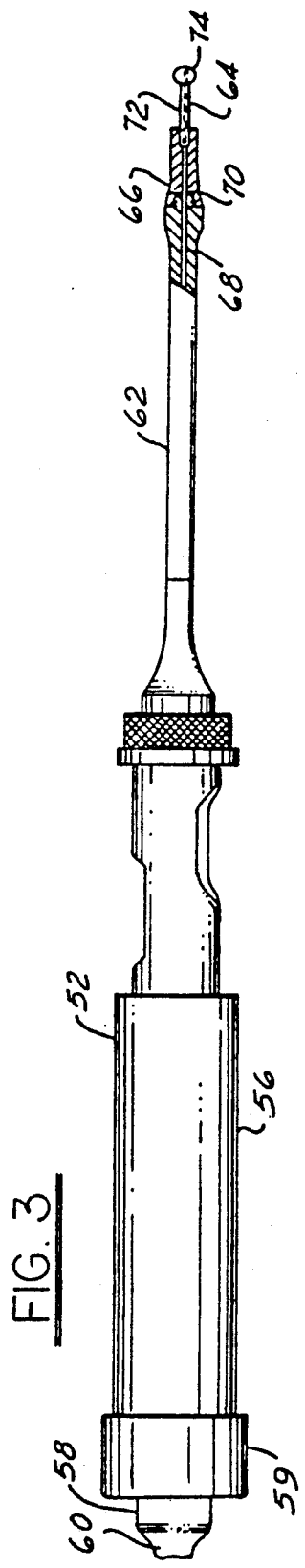
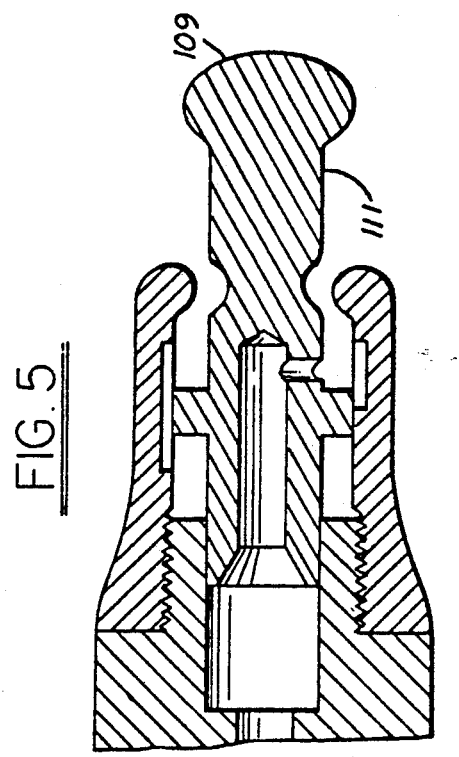
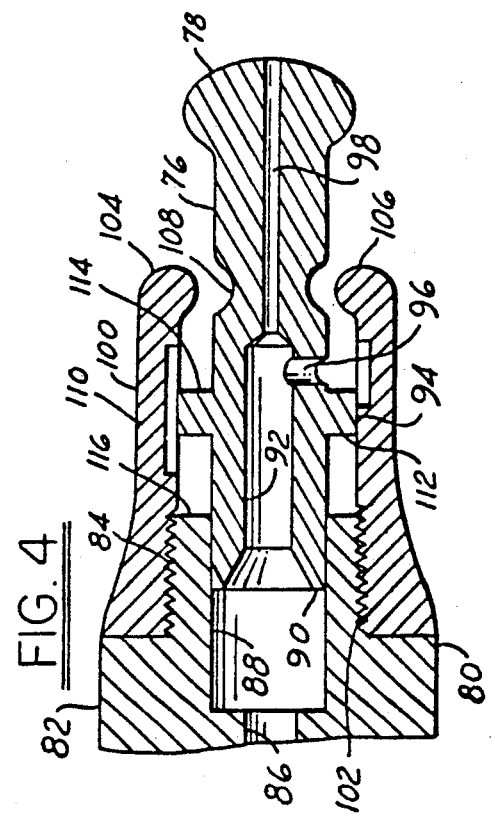

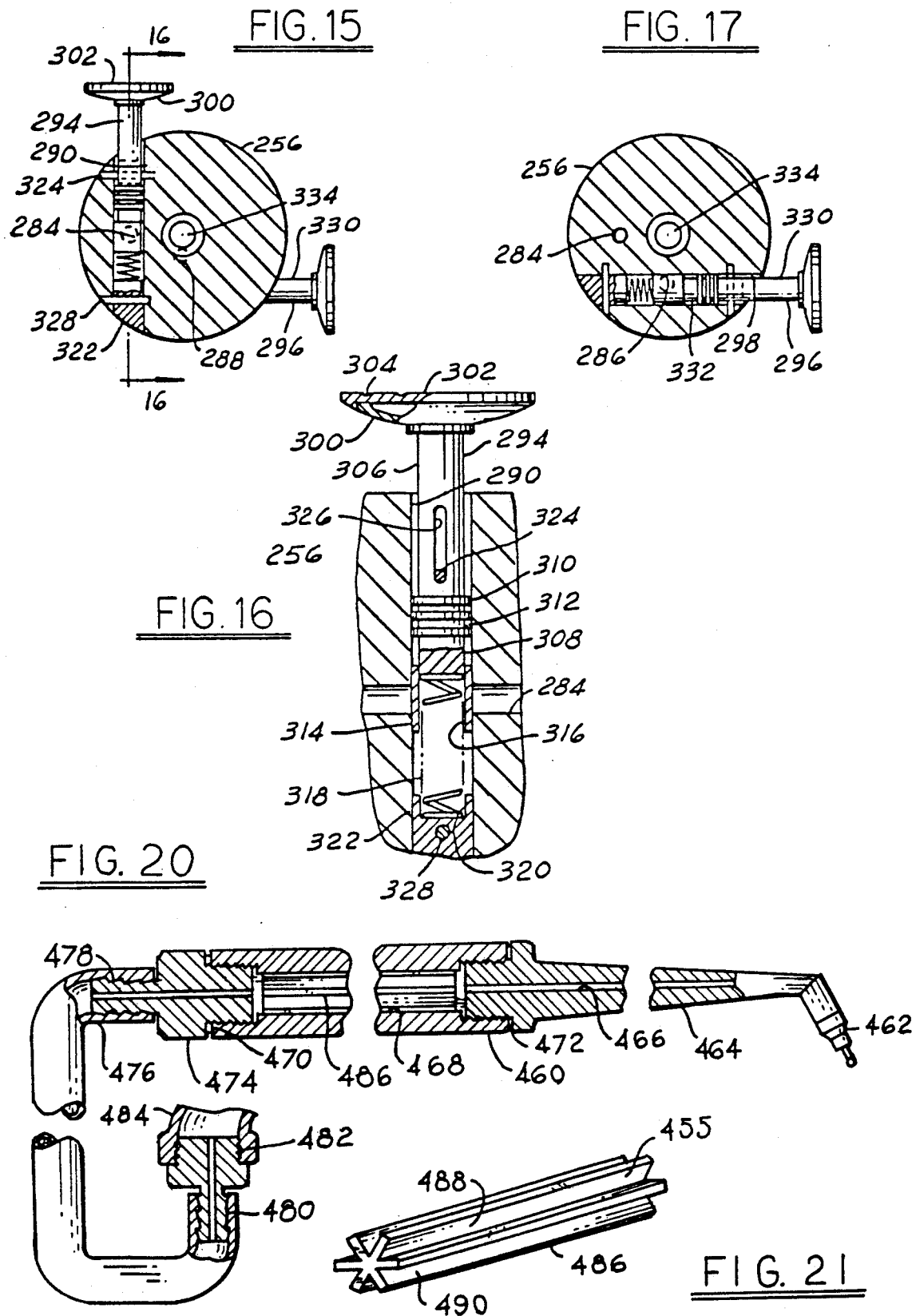

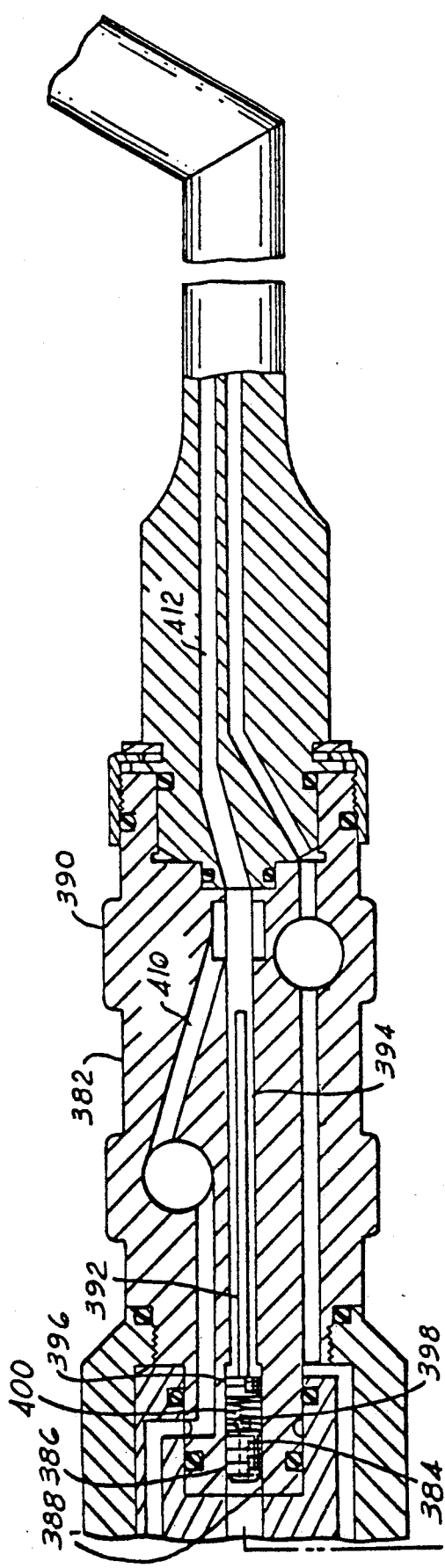
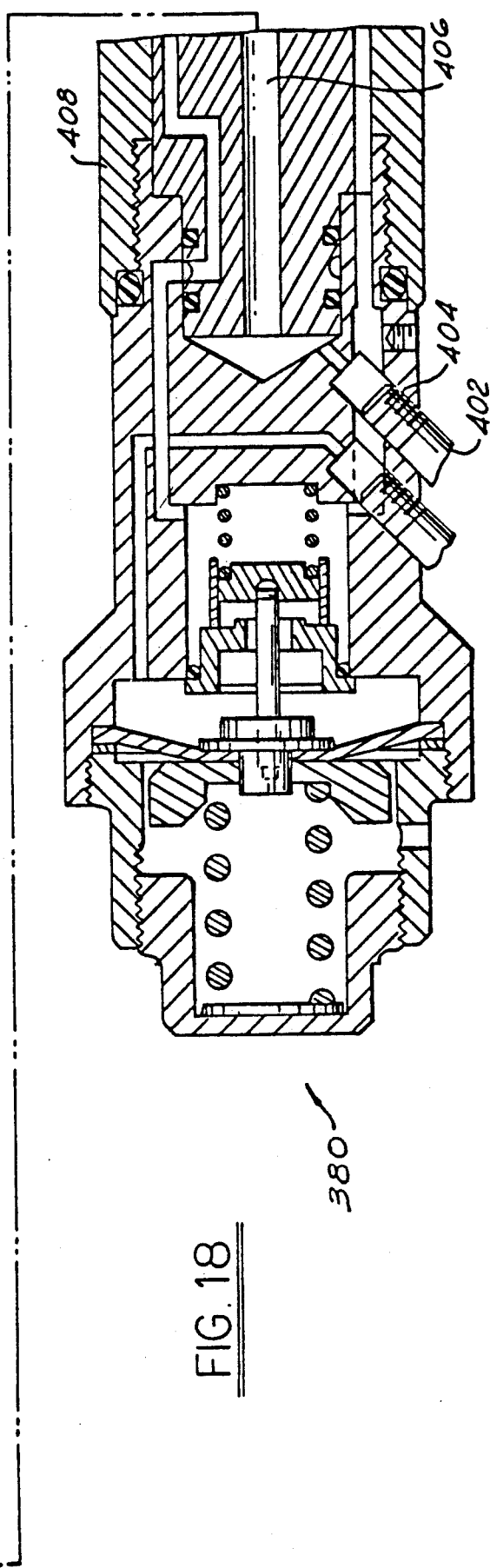
FIG. 18

TISSUE SEPARATOR METHOD

CROSS REFERENCE TO RELATED APPLICATION

This Application is a Contiuation in Part of application Ser. No. 582,971, filed Nov. 21, 1983, now U.S. Pat. No. 4,709,697, which is a Contiuation of appliction Ser. No. 214,006, filed Dec. 9, 1980, now abandoned, which is a Continuation in Part of application Ser. No. 103,206, filed Dec. 13, 1979, now U.S. Pat. No. 4,357,940.

BACKGROUND OF THE INVENTION

1. Field of the Invention

The invention relates to a new surgical dissection method based on tissue separation, and relates more specifically to using a tissue pneumatic or hydraulic separator for directing a suitable fluid, such as nitrogen gas under pressure or a liquid incorporating specific biological properties, at a controlled fluid pressure through a calibrated orifice or jet in a controlled direction toward tissue or tissues to be separated, preferably along natural cleavage planes, either before separation or removal of tissue or organ such as in dederminization and/or desepidermtation, and also relates to the tissue pneumatic separator with which the method of the invention is practiced for tissue separation or organ removal instead of blunt or sharp dissection, for tissue cleaning and for tissue preparation or treatment with jets of fluids or slurries that may be medicinal.

2. Description of the Prior Art

In the past, methods for separating tissue such as tumor sacs or membranes from surrounding healthy tissue or for specifically organ, nerve or blood vessel dissection have usually included using cutting devices and/or high frequency vibrating structures and/or cauterizing devices such as electric knives or lasers to separate the tissue. Such methods also used cutting devices, such as scalpels, and have sometimes caused undesirable damage to and bleeding from tissue being separated or from surrounding tissue. Further more high frequency vibrating heads or electrical knives often use cumbersome umbilical connections to nearby generators with electrical power inputs and are very expensive. All such prior methods for separating tissue have caused unnecessary damage to the tissue or organs being separated.

SUMMARY OF THE INVENTION

In its simplest form, the invention comprises a tissue separator approximately the size of a felt pen having a mechanical nudging tip thereon for physically nudging the tissue to be separated to provide tissue separation. In a preferred embodiment, the invention is a tissue pneumatic separator wherein a suitable fluid at a controlled pressure flows through a calibrated orifice in a floating tip in variously controlled directions to separate or cleanse tissue rapidly and accurately without damage to the tissue or surrounding membranes. The tip of the tissue pneumatic separator of the invention floats on balanced cushions of the fluid and is biased thereby outwardly of the stem to limit the nudging pressure applied by the floating tip, and thus prevent accidental injury.

In use of a sophisticated embodiment of the tissue pneumatic separator, nitrogen gas is variably controlled in pressure and may be passed to the floating tip through at least two separate controls operable either by a surgeon's thumb or his forefinger. In one modification of the tissue pneumatic separator of the invention, gas used in the separation of tissue and flowing forward through the calibrated orifice of the floating tip is controlled by the surgeon's forefinger while moisturizing fluid is passed forward around the floating tip of the tissue pneumatic separator and controlled by the physician's thumb. In another modification of the tissue pneumatic separator, the gas utilized to separate tissue and flowing forward through the calibrated orifice of the float tip is controlled by the surgeon's forefinger while excess fluids in the area of the tissue being separated may be withdrawn rearward by suctioning around the floating tip of the tissue pneumatic separator under control of the surgeon's thumb.

In a preferred use of the invention, tissue is separated by nitrogen gas passing through a floating tip of the tissue pneumatic separator, which tip may also be used to nudge the tissue being separated under a controlled and balanced gas pressure. The gas pressure may be variable, measurable, and predictable. Other gases such as carbon dioxide and liquids such a water may be utilized in practicing the method of the invention if desired and may be preferred in specific applications.

In further modifications of the method of the invention, moisturizing fluids may be passed to the tissue being separated at the same time the tissue is being separated by gas directed thereon and/or physical nudging. Also fluid, organic material or other debris may be removed from the area of the tissue being separated in accordance with the method of the invention at the same time tissue separation is being accomplished or alternately therewith. The fluid material may also be passed through or around the floating tip of the tissue separator either alternately or simultaneously.

In a particular embodiment of the invention suitable for dental use, the fluid material is water, which is variably regulated and may be pulsed. The water may be obtained from a municipal water supply through a faucet or from a pressurized container.

Also, in the method of the invention the tissue separator structure may include a body portion and the fluid medium is passed over a high surface to fluid interacting, soap-like, replacable cartridge. The cartridge is made of at least one of an abrading, cleansing, antiseptic, astringent, flavoring, fungicidal and bacteriocidal matter within the body portion prior to directing the water at the tissue.

BRIEF DESCRIPTION OF THE DRAWINGS

FIG. 1 is a partly broken away, elevation view of a tissue separator constructed in accordance with the invention for effecting the method of the invention.

FIG. 2 is a partial elevation view of a modification of the tissue separator illustrated in FIG. 1 showing a tip extending at an angle to the longitudinal axis of the separator.

FIG. 3 is a partly broken away, elevation view of a tissue pneumatic separator constructed in accordance with the invention for effecting the method of the invention.

FIG. 4 is an enlarged section view of a floating tip for use with the tissue pneumatic separator of FIG. 3.

FIG. 5 is an enlarged section view similar to that of FIG. 4, showing a modified floating tip.

FIG. 15 is an enlarged cross section of the valve unit of the tissue pneumatic separator of FIG. 10, taken substantially on the line 15—15 in FIG. 10.

FIG. 16 is an enlarged partial cross section of the valve unit of the tissue pneumatic separator of the invention shown in FIG. 10, taken substantially on the line 16—16 in FIG. 15.

FIG. 17 is an enlarged cross section of the valve unit of the tissue pneumatic separator of FIG. 10, taken substantially on the line 17—17 in FIG. 10.

FIG. 18 is a broken longitudinal section of a modification of the tissue pneumatic separator illustrated in FIG. 10.

FIG. 20 is a broken away elevation view of still another modification of the tissue pneumatic separator of the invention having a floating tip and including a cartridge of soap-like material therein.

FIG. 21 is a persepctive view of the cartridge of soap-like material shown in FIG. 20.

DESCRIPTION OF THE PREFERRED EMBODIMENT

Figure 7:
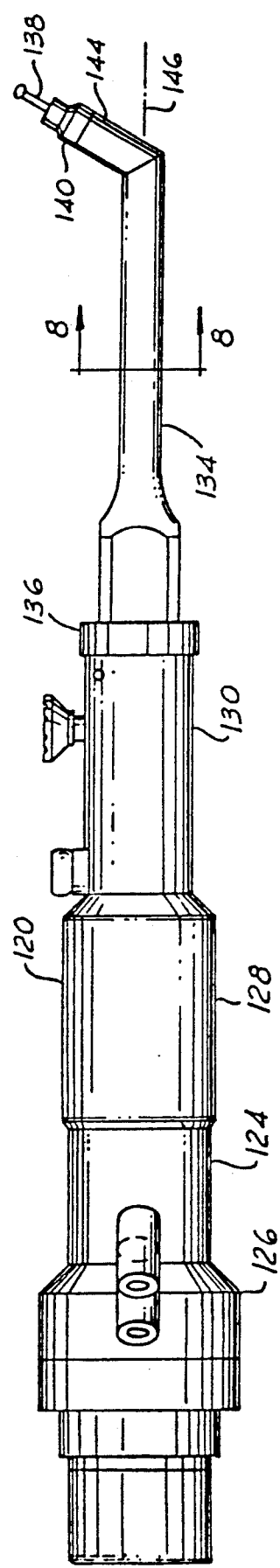
FIG. 7 is an elevation view of a more sophistricated embodiment of the tissue pneumatic separator of the invention for practicing the method of the invention.

As shown in FIG. 1, the simplest embodiment of the tissue separator of the invention is a mechanical nudger or tissue separator 10 including a hollow handle 12, a stem le secured to the handle 12 by stem retainer 16 and further including tip 18 and tip retainer 20. An end cap 24 is provided on the hollow handle 12 as shown.

The hollow handle 12 is a generally cylindrical and has the thumb and forefinger depressions 26 and 28 therein. The end cap 24 is secured to the hollow handle 12 by convenient means such as screw threads 30. Similarly, the stem 14 is secured to the handle 12 by the stem retainer 16 which is provided with a radially extending flange 32 engaging a radially extending flange 34 on the stem 14. The stem retainer 16 is secured to the end of the handle 12 by convenient means such as the screw threads 36 shown in FIG. 1. See, for example, details of FIG. 10 for specific structure providing finger-tight preset friction using O-ring sealing members.

The tip 18 is provided with screw threads 38 on the inner end thereof and is provided with a bulbous outer end 40. Alternatively, the tip 20 may be provided with an interference fit. If the tip and stem are plastic, the interference fit may be followed by an ultrasonic weld. The bulbous other end 40 is utilized to gently nudge tissue to be separated to cause separation thereof. The tip retainer 20 is provided with threaded recesses 42 and 44 in the opposite ends thereof for receiving the threaded end 38 of the tip 18 and the threaded projection 46 on the end of the stem 14.

In use, the tissue separator 10 is held by the handle 12 by a surgeon having his thumb in the depression 26 and his finger in the depression 28 and the tissue to be separated is gently nudged with the bulbous end 40 on the tip 18.

The entire stem 14, tip retainer 20, and tip 18 may be a throw-away item for use in only a single surgical procedure.

Further, as shown best in FIG. 2, the stem 14 may be bent at an angle to facilitate tissue engagement with the bulbous end 40 and better viewing for the surgeon. As shown in FIG. 2, the axis 50 of the tip 18 may make an angle of, for example, 60° with the axis 48 of the stem 14. The particular angle of 60° is, however, not critical but has been found to be particularly useful. Also, while the stem 14 is preferably bent to extend upward with the tissue separator 10 in use, it may be bent and/or rotated about its axis in any desired direction.

In this regard, it will be understood that the stem may be of resilient, flexible or malleable material and may be bent as desired. Thus, for example, the stem may be constructed of stainless steel, plastic or aluminum, as desired.

In the modified tissue pneumatic separator 52 shown in FIG. 3, a fluid medium under pressure is connected to the hollow handle 56 through the coupling 58 on end cap 59 and the flexible conduit 60 from a source of fluid medium under predetermined head pressure, not shown. Further, the stem 62, the tip 64 and the tip retainer 66 of the tissue pneumatic separator 52 are provided with axially aligned, axially extending passages 68, 70 and 72, respectively, in communication with the fluid medium from the hollow handle 56.

Thus, in use of the tissue pneumatic separator 52, the fluid medium under pressure, which may for example be nitrogen gas or other fluid non-injurous to the tissue being separated and its vascular system, is utilized at selected head pressures to separate tissue such as tumor sacs from adjacent healthy tissue by blowing the fluid medium through the end of the tip 64 at the tissue at the interface between the tissue to be separated. The tissue separation may also be aided by gently nudging physically with the bulbous end 74 of the tip 64.

In a more sophisticated tissue pneumatic separator, as shown in FIGS. 4 and 5, the tip 76 is floated on a cushion of the fluid medium whereby the possible pressure applied during mechanical nudging with the bulbous tip 78 is controlled in accordance with the pressure of the fluid medium.

As shown in FIG. 4, the end 80 of the modified stem 82 is provided with a threaded extension 84 as before and an axially extending passage 86 is provided extending through the stem 82 in communication with a source of fluid medium under pressure. A recess 88 is also provided in the end 80 of the stem 82.

The tip 76 is generally cylindrical and has an inner end 90 positioned within the recess 88 for axial reciprocation therein, which end 90 has an axially extending recess 92 therein, as shown. The other end 78 of the tip 76 is a bulbous tissue separator as indicated previously. An annular radially extending flange ecting as a piston 94 is provided centrally of the tip 76, as shown.

A calibrated radially extending passage 96 extends from the recess 92 in the end 90 of the tip 76 through the outer surface of the tip 76 positioned as shown. A further axially extending passage 98 or calibrated orifice extends through the bulbous outer end 78 of the tip 76. Particularly useful diameters for the passage 98 with fluid medium pressures from 3.5 to 25 p.s.i. have been found to be .016, .025 and .032 inches.

The tip retainer 100 is generally cylindrical and has an internally threaded inner end 102. The outer end 104 is terminated in a radially inwardly extending generally flared, bulbous annulus 106 generally in radial alignment with an annular groove 108 in the tip 76. A plurality of angularly separated, axially and radially extending slots 110 are provided around the inner surface of the tip retainer 100 as shown in FIG. 4 to permit fluid medium under pressure to bypass the annular flange 94 on the tip 76 to cause the tip 76 to float on the fluid medium in use.

Opposing flat surfaces 95 and 97 are provided on tip retainer 100 to facilitate assembly and disassembly of the tip retainer 160 on stem 62.

In use of a tissue pneumatic separator such as that illustrated in FIG. 3 having a floating tip 76 as illustrated in FIG. 4 thereon, the fluid medium passes through the passage 86 through the recess 88 and recess 92 radially outwardly through the passage 96 and through the slots 110 to provide a force, tending to push the tip 76 to the right in FIG. 4, equal to the force due to the pressure acting on the surface of the end 90 of the tip 76 and the pressure on the side 112 of the annular flange or piston annular surface 94.

This force is counteracted by the pressure of the fluid medium on the side 114 of the annular flange or piston 94 and pressure on the bulbous end 78 of the tip 76 due to physical nudging with the tip 76 to separate tissue and/or any back pressure which might be provided on the end 78 of the tip 76 due to the fluid medium under pressure exiting through the calibrated orifice 98 of the tip 76.

The passages 96 and 98 and to a lesser extent the areas of the slots 110 and annulus between the groove 108 and annulus 106 determine the load at which the tip 76 will retract when nudged against tissue due to the cushion of gas existing between the tissue and the bulbous tip or nudged directly via physical contact on the tissue. This is why the tip has been designed a floating tip. That is to say, all these predetermined factors establish the load on the end 78 of the tip 76 which will cause the tip to retract and move to the left in FIG. 4. Typically a nudging load with a tip jet orifice of .031 can be as little as 4 grams under a head pressure of 8 p.s.i.

It will be understood that movement to the right of the tip 76 is limited by the bulbous annulus 106 on the tip retainer 100 while the movement to the left of the tip 76 is limited by the outer end surface 116 of the stem 82.

Further, it will be understood that with the particular floating tip structure illustrated in FIG. 4 that the fluid medium exiting through the calibrated orifice 98 will produce a thin pencil of relatively high pressure fluid medium for separating tissue while an annulus of lesser pressure will be provided between the bulbous end 106 of the tip retaining structure 100 and the annular groove 108 about the stem 76. The lower pressure annulus is particularly useful in continuously clearing the area around the tissue being separated.

The modified floating tip structure illustrated in FIG. 5 is in all respects similar to that shown in FIG. 4 with the single exception that the axial passage 98 has been eliminated from the end 109 of the tip 111. With such structure as that shown in FIG. 5, the tissue separating may be accomplished by mechanical nudging of the tissue to be separated by the bulbous end 109 of the tip 111 which nudging is limited by the floating pressure of the tip 111. Such limiting of the nudging pressure due to the floating tip prevents injury to the tissue being separated.

Figure 6:
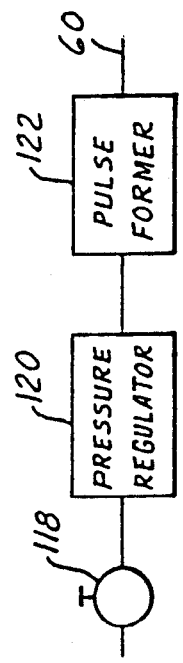
FIG. 6 is a block diagram of hydraulic structure of the invention as shown in FIG. 3 in a dental application.

While the structure of FIG. 3 is intended in its preferred use to be utilized to separate tissue, particularly in conjunction with the floating tips as illustrated in FIGS. 4 and 5, other uses therefor are contemplated. Thus, for example, the structure of FIG. 3 may be utilized by dentists or others for cleaning teeth and between teeth. In such application, as shown in FIG. 6, the flexible conduit 60 may be connected to a source of water under pressure such as a normal hot and cold water mixing faucet 118 directly, if desired, or as shown in FIG. 6 through a water pressure regulator 120 and-/or a pulse forming structure 122. With the structure of FIG. 3 so connected, the water under pressure exiting from the tip 72, or more preferably from the floating tip 76 illustrated in FIG. 4, when directed at the teeth and gums may be utilized to wash away undesirable accumulation of food particles and the like from the teeth and gum area. The floating tip literally rides over the teeth following their contour.

The tissue pneumatic separator 120 illustrated in FIGS. 7–17 is more sophisticated than that shown in FIGS. 3–6. As shown in FIG. 7, the tissue pneumatic separator 120 includes a body assembly 124 having a pressure regulator subassembly 126 and a manifold subassembly 128. A valve unit 130 is provided between the stem 134 and the manifold subassembly 128. The stem 134 is again secured to the valve unit 130 by means of stem retaining structure 136 and a floating tip 138 is connected to the stem 134 by tip retainer 140.

The stem 134, which again may be disposable, is provided with an axially extending passage 142 through which fluid medium is passed to the tip 138 and with a parallel radially displaced passage 144 through which fluid medium is passed towards or withdrawn from around the tip 138, as will be seen subsequently. Also, as particularly shown in FIG. 9, the stem 148 may be straight or the end 144 thereof may be displaced at an angle from the longitudinal axis 146 of the tissue pneumatic separator 120, as before.

Figure 10:
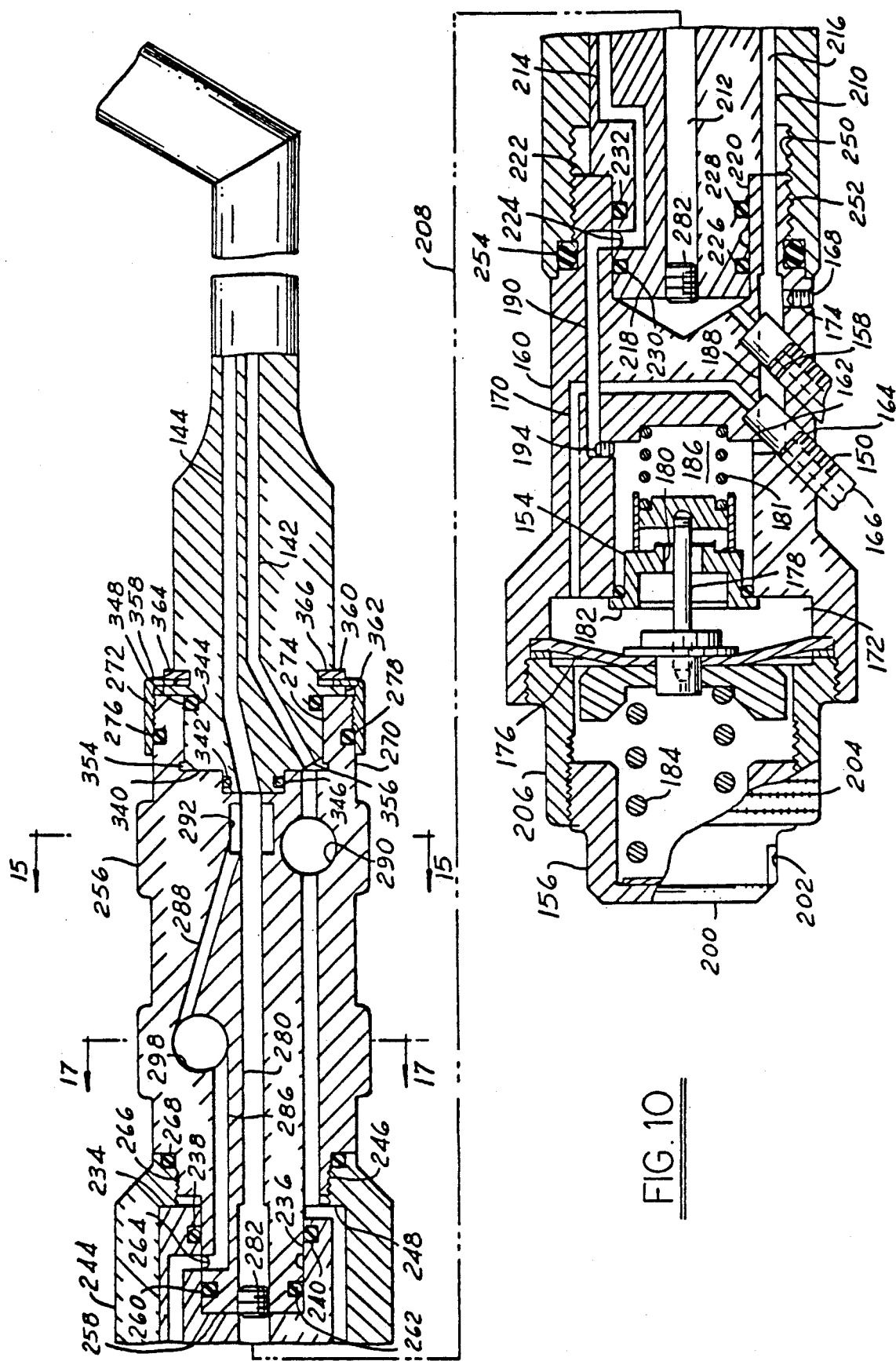
FIG. 10 is a enlarged broken longitudinal section view of a portion of the tissue pneumatic separator shown in FIG. 7.

The outer hollow cylindrical member 244 of the manifold subassembly 128, as shown best in FIG. 10, includes the inwardly extending threaded flange 246 thereon which provides an abutment 248 on which end 234 of the inner cylinder 210 rests. The other end of the outer cylinder 244 is internally threaded at 250 and mates with the externally threaded end 222 of the body member 160 of the tissue pneumatic separator 120. An annular O-ring seal 254 is provided between the body member 160 and the outer cylindrical member 244 as shown.

Figure 9:
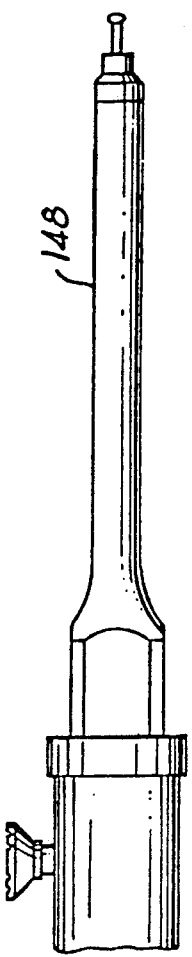
FIG. 9 is a partial elevation view of a modification of the tissue pneumatic separator illustrated in FIG. 7 showing a straight stem.
Figure 8:
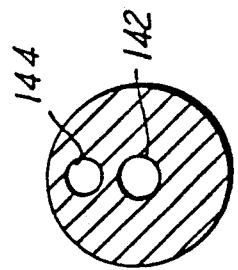
FIG. 8 is an enlarged cross section of the stem of the tissue pneumatic separator illustrated in FIG. 7, taken substantially on the line 8—8 in FIG. 7.

For clarity, the straight stem has been numbered 148 in FIG. 9 to distinguish it from the stem 134 having an angularly displaced end 144. All other reference numerals in FIG. 9 are the same as those used in FIG. 7 for the same parts and their functions disclosed therein.

As shown in more detail in FIG. 10, the pressure regulator subassembly 126 of the body assembly 124 includes inlet structure 150 for a fluid medium under pressure, pressure control structure 154, variable indicator structure 156 for the pressure control structure 154, fluid outlet structure 158, and regulator fluid pressure tap 152, all secured to or part of body member 160 which is cylindrical and has the general longitudinal section shape illustrated best in FIG. 10.

Fluid pressure tap 152 which includes threaded opening 174 and plug 168 allows assembly insertion of pressure inspection means or means for visual display of regulated pressure, if so desired, by the operating surgeon. It may also be used by the manufacturer to calibrate the built-in pressure regulator 154 and indicator 156 as documented later on.

As shown in FIG. 10, the fluid medium inlet structure 150 includes a recess 162 in the body member 160 having a threaded outer end 164 for receiving a flexible conduit 166 which provides an umbilical cord through which fluid medium such as nitrogen gas under pressure is passed into the tissue pneumatic separator 120. Typical gas pressure from an externally controlled source at inlet structure 150 is 50 p.s.i.

The pressure regulator control structure 154, as shown, includes an annular diaphragm 176 having a needle valve 178 secured thereto for metering the pressurized fluid medium through the opening 180 in the valve member 182. As shown, the position of the needle valve 178 is controlled by the force of bias spring 181 and the adjusting spring 184 which through mechanical connecting structure act on the opposite ends of the needle valve 178.

Thus, in accordance with the axial position of the needle valve 178 in the opening 180, the pressure from the chamber 172 is dropped in a controlled manner into the chamber 186, from whence it is passed into the manifold subassembly 128 through the passage 188 in the body member 160. Typically, regulated pressure levels of 3 p.s.i. to 35 p.s.i. are obtained and used in chamber 186.

The pressure in the chamber 186 may also be passed into the manifold subassembly 128 through the passage 190 in the pressure regulator subassembly 126 if desired in different embodiments of the tissue pneumatic separator 120, as will be seen subsequently. Thus, the plug 194 may be in position in the passage 190 or not depending on the desire for pressurized fluid medium at certain places, and in the floating tip having certain characteristics, as will be seen subsequently.

The variable pressure indicator structure 156 includes a rotary end cap 200 having the indicator dot 202 thereon. The indicator dot 202 functions in conjunction with the graduations 204 marked on the cylindrical member 206 secured to the body member 160 to indicate the exact head pressure which the pressure control structure 154 provides in the chamber 186. Thus, the pressure of, for example, 50 p.s.i. in the chamber 172 may be reduced to 5 p.s.i. or less in the passages 188 and 190 and the value of the pressure is indicated by the graduations 204 and the position of the dot 202 on the rotary end cap 200 and the number of rotations of the end cap 200. As said previously, calibration can be preformed by using a pressure gauge inserted in the fluid pressure tap 152 threaded opening 174.

Thus, for the first 360° of rotation of end cap 200, the outer graduation scale is utilized in conjunction with the dot 202 to provide a pressure reading within the chamber 186 of up to about 18 p.s.i. For the next 360°, the center graduation scale is utilized in conjunction with the dot 202 to provide an indication of the pressure in the chamber 186, and so on through the number of permitted rotations of the rotatable end cap 202. The pressure within the chamber 186 is thus completely variable in accordance with the angular position of the rotatble cover 200 over several complete revolutions, generally two, thereof.

The manifold subassembly 128 as shown in FIG. 10 extends between the pressure regulator subassembly 126 and the valve unit 130, as shown in FIG. 7. The manifold subsection 128 is broken in FIG. 10 with the connection between the broken parts thereo- shown by the construction line 208.

More specifically, the manifold subassembly includes an inner cylinder 210 having an axial passage 212 extending therethrough. Further, cylinder 210 has a passage 214 and a groove 216 imbedded on the outer surface of the inner cylinder and extending longitudinally over substantially the entire length thereof, thus creating a second passage for the fluid medium in conjunction with the outer cylinder 244 considered subsequently.

Fluid medium is passed to the valve unit 130 through the passages 214 and 216, while either a fluid medium at a different pressure or a moisturizing liquid may be passed through the central passage 212, or fluid from tissue being separated may be withdrawn through the passages 212 to be passed out of the tissue pneumatic separator 120 through the outlet structure 158.

As shown in FIG. 10, the reduced diameter end 218 of the inner cylinder 210 of the manifold subassembly 128 is positioned within the recess 220 in the end 222 of the body member 160 of the pressure regulator subassembly 126. An annular groove 224 is provided on the outer surface of the inner cylinder 210 at the end 218 thereof for circumferentially distributing fluid medium from the passage 190 to insure that the fluid medium passes into the passage 214 from the passage 190 regardless of the relative angular position of the inner cylinder 210 and the body member 160. Sealing O-rings 226 and 228 extend annularly around the end 218 of the inner cylinder 210 in grooves 230 and 232 provided on opposite sides of the annular recess 224 as shown in FIG. 10.

The end 234 of the inner cylinder 210 of the manifold subassembly 128 is provided with recess 236 therein having the internal annular groove 238 therearound in which the O-ring seal 240 is positioned as shown in FIG. 10.

The outer hollow cylindrical member 244 of the manifold subassembly 128 as shown best in FIG. 10 includes the inwardly extending threaded flange 246 thereon which provides an abutment 248 on which end 234 of the inner cylinder 210 rests. The other end of the outer cylinder 244 is internally threaded at 250 and mates with the externally threaded end 222 of the body member 160 of the tissue pneumatic separator 120. An annular O-ring seal 254 is provided between the body member 160 and the outer cylindrical member 244 as shown.

Valve unit 130 as illustrated in FIG. 10 includes the valve body member 256 which is generally cylindrical. End 258 of the body member 256 includes a sealing O-ring within an annular groove 262 therearound. End 258 of valve body member 256 is provided with annular groove 264 therearound to insure communication of pressure medium between passage 214 and passage 286. The valve unit body member is secured to the outer cylinder 254 of the manifold structure 128 by means of the threaded end portion 246. An O-ring seal 268 is provided between the valve unit body member 256 and the outer cylinder 244 of the manifold subassembly 128.

The other end 270 of the valve body member 256 is provided with external threads 272 therearound and with a recess 274 therein as shown. An annular groove 276 extends around the outer surface of the end 270 of the valve body member 256 as shown in which the annular sealing ring 278 is positioned.

An axially extending passage 280 is provided in the valve body member 256. In the modification of the tissue pneumatic separator 120 shown in FIG. 10, the passage 280 is provided with a plug or plug function 282 at end 258 of the valve unit body member 256, as shown.

The valve unit body member 256 is further provided with passage 284 extending axially therethrough radially displaced from the passage 280. In addition, passages 286 and 288 are provided in the valve body member 256 extending respectively between annular groove 264 and the valve recess 290 and the annular recess 292 surrounding the passage 280, as shown.

Valves 294 and 296 are provided in valve recesses 290 and 298 between passages 286 and 288 and in passage 284, as shown. The valves are entirely similar and are shown best in FIGS. 15, 16 and 17. The valves 294 and 296 may be constructed of suitable plastic having a desirably low coefficient of friction such as Teflon which is autoclavable, or Delfrin which is not autoclavable, but which may be chemically or otherwise sterilized.

As shown, the valve 294 includes a head 300 having a plastic cap 302 thereover with annular grooves 304 therein to prevent slippage of a surgeon's fingers therefrom and the valve stem 306 extending from the valve head 300, into the recess 290. The valve stem 306 has the metering annular recess 308 extending therearound as shown best in FIG. 16 and is provided with a plurality of sealing lands 310 between the metering groove 308 and the head 300 as shown in FIG. 16. If necessary, a sealing packing 312 is provided between some of the lands 310.

The end 314 of the valve stem 306 has a recess 316 which is adapted to receive the spring 318 extending between the recess 316 and a similar recess 320 in the cup-shape bottom valve member 322. The spring 318 urges the valve stem 306 out of the recess 298.

The valve stem 306 is maintained in the recess 298 by the pin 324 positioned in the slot 326 in the stem 306. The length of the slot 326 equals the travel of the valve 294. Pin 328 is provided to retain the cup-shape spring retainer 322 in recess 290.

As will be seen from a view of FIGS. 15 and 17, the passages 290 and 298 extend completely through the valve body member 256 and the openings for the pins 324 and 328 are symmetrically positioned in the passage whereby the valves 294 and 296, and in particular the valve 296, may be reversed, that is, placed on the opposite side of the valve body member 256 to permit use of the tissue pneumatic separator by a left-handed operating surgeon.

Thus, in operation of the valve structure 294, when the valve stem 306 is depressed against the bias of the spring 318, the annular metering groove 308 is aligned with the passage 284 to permit fluid medium to flow through the valve unit 130 in the passage 284.

Similarly, when the valve stem 330 is moved to the left in FIG. 17, the metering groove 332 is aligned with the passages 286 and 288 whereby fluid medium is passed from the passage 286 to the passage 288.

As shown best in FIGS. 15 and 17, the passages 284 and 286 are displaced radially from the central passage 288 and are angularly displaced from each other about the longitudinal axis 146 of the tissue pneumatic separator 120 by 90°. For economy sake, the passages in the body assembled and the metering unit 256 are shown in the same plane in the longitudinal section of FIG. 10 and therefore in the section of FIG. 10 are shown out of position.

As previously considered, the stem 134 of the tissue pneumatic separator 120 may be a disposable stem suitable for a single surgical procedure, after which it may be discarded. Alternatively, of course, the stem 134 may be made of suitable material such as Teflon for placing in an autoclave or other sterilizing atmosphere for repeated re-use, as considered above. Also, as set forth above, the stem 134 may be of any desired length and may be constructed of rigid material such as stainless steel or resilient, flexible or maleable material such as steel, plastic or aluminum.

The end 340 of the stem 134 shaped as shown is positioned in the recess 274 in the valve unit body member 256 with annular sealing rings 342 and 344 in grooves 346 and 348.

As shown, the stem 134 is provided with the radially displaced passage 144 extending therethrough and the axial passage 142. The passage 144 is in communication directly with passage 280 in the valve unit 130, while the passage 142 is in communication with the passage 284 in valve unit 130 through the annular space 354 provided by the beveled surface 356 on the end 340 of the stem 134.

Stem 134 is secured to the valve unit 130 by the stem-retaining structure 136. Stem-retaining structure 136 includes the annular flanged member 358 having the axial cross-section as shown in FIG. 10, and the C-shaped clamp 360. In assembly, the annular member 358 is sleeved over the stem 134 and abuts the annular flange 362 on the stem 134 to secure the stem 134 against the end surface 364 of the valve body 256 on threaded engagement of member 358 with the threads 272 on the valve body member 256. The snap ring 360 is then inserted in the annular groove 366 in the stem 134 to lock the member 358 in place.

The stem-retaining structure 136 having the structure shown in FIG. 10 may thus be secured to the valve body member 256 with the annular member 358 finger tight. The stem 134 is rotatable about its axis while a seal between the valve body member 256 and the stem 134 is maintained. The seal between body member 256 and the stem 134 also provides friction, which allows orientation of the angle type tip and insures it will stay put as directed by the operator.

Figure 11:
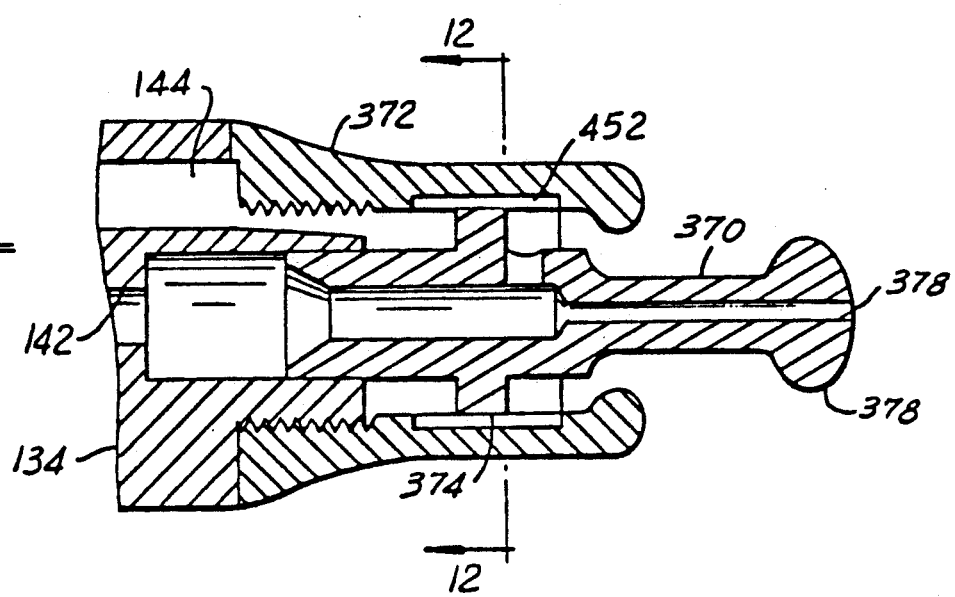
FIG. 11 is an enlarged longitudinal section view of the end of the stem, the floating tip, and tip retainer of the tissue pneumatic separator illustrated in FIG. 10.
Figure 12:
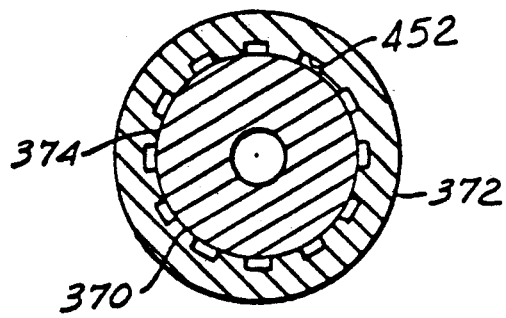
FIG. 12 is a cross section of the floating tip and tip retainer illustrated in FIG. 11, taken substantially on the line 12—12 in FIG. 11.

Floating tip 370 is secured on the end of the stem 134 by tip retainer structure 372 as shown best in FIG. 11. The floating tip 370 and tip retainer 372 as shown in FIGS. 11 and 12 are the same as the floating tip 76 and tip retainer 100 shown in FIG. 4 and will not therefore be considered again in detail. It will be noted, however, in conjunction with FIG. 11, that the passage 144 from the stem 134 is in communication with the area behind the annular flange 374 on the tip 370.

Thus, in operation of the tissue pneumatic separator 120 shown in FIGS. 7–12 and FIGS. 15, 16 and 17 as described immediately above, the pressure of the fluid medium tending to push the floating tip to the right in FIG. 11 is or may be determined, not only by the pressure controlled by the valve 294, but is also controlled in accordance with the pressure in the passage 144 under control of the valve 296.

Pressure in the pasage 142 will be the pressure from chamber 186. Pressure in passage 144 will, however, vary depending on which of plugs 194 and 282 are in place and what, if any, fluid medium is connected to outlet structure 158. Thus, with both plugs 194 and 282 in place, no fluid medium will be present in passage 144. Therefore, only calibrated orifice 378 is in use and cleaning action is obtained through gas or liquid fluid escaping through passage 375 as considered in conjunction with floating tip 76 of FIG. 4.

With only plug 282 in place, the pressure in passage 144 will be that in chamber 186 also. With only plug 194 in place, the pressure in passage 144 will be that connected into outlet structure 158.

In any event, there is provided in accordance with the fluid medium pressure operating on the floating tip 370, a pressure tending to move the floating tip 370 to the right in FIG. 11, as before. The force available to effect tissue separation with the bulbous end 376 of the tip 370 is then the residual force necessary to move the tip 370 to the left in FIG. 11 in opposition to the fluid pressure forces acting on the tip 370 from the passages 142 and 144.

Again, a thin pencil of fluid medium will pass through the passage 378 in the tip 370 to impinge upon and tend to force separation of tissue immediately in front of the bulbous tip 376, as before. Also, as before, a fluid medium pressure will be exerted around the outside of the tip 370 to clear away the area about the tissue being separated if one of the plugs 194 and 282 are removed and pressure is then present in passage 144.

With such operation, it will be noted that the operating surgeon is in complete control of the fluid medium pressures in passage 142 and 144 due to the inclusion of the valves 294 and 296 in the tissue pneumatic separator 120. In this respect, the tissue pneumatic separator 120 is considerably more sophisticated than the tissue pneumatic separator 52 illustrated in FIG. 3, if so required by the surgical procedure.

In the modified tissue penumatic separator structure 380, as shown best in FIG. 18, the valve unit 382 is modified by replacing the plug 282 in the tissue pneumatic separator 120 with a plug 384 having and axially extending passage 386 therethrough positioned in the axially extending threaded recess 388 in the valve body member 390.

Further, the valve unit 382 includes an aspirating pipe 392 positioned in the axial passage 394 and held therein by the threaded end 396 thereon in recess 388. A check valve 398 is urged into closing relation to the passage 386 through the plug 384 by the bias spring 400, as shown best in FIG. 18, to prevent fluid under pressure in passage 412 from passing upstream.

With such structure, a source of moisturizing fluid such as water is connected through umbilical cord 402 in outlet structure 404 whereby water is placed in passage 406 of the manifold assembly 408.

With the modified tissue pneumatic structure 380 shown in FIG. 18, with the proper differential between the spring pressure on the check valve 398 and the water pressure in the passage 406, the valve 398 will be caused to open when a sufficient vacuum is provided at the end of the aspirating pipe 392 due to a venturi effect produced by the fluid medium from the passage 410 passing through the passage 410 and into the passage 412.

The moisture from the aspirating pipe 392 is thus mixed with the fluid medium such as nitrogen gas in the passage 412 and passed around the floating tip 370. Thus, with the modified tissue pneumatic separator 380 shown in FIG. 18, the tissue being separated may be moisturized under separate thumb control of valve 296 while it is being separated under forefinger control of the other valve 294.

Figure 19:
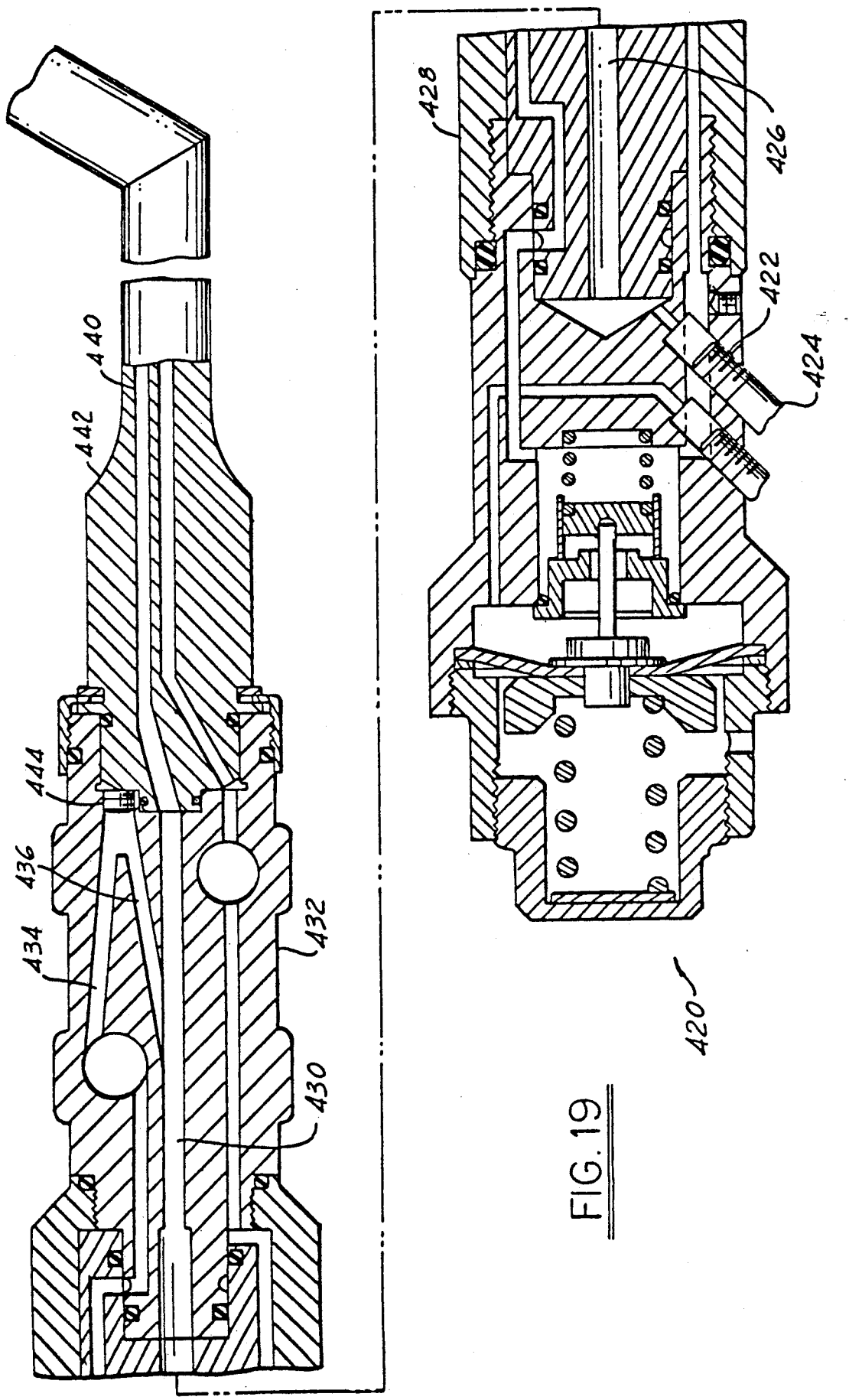
FIG. 19 is a broken longitudinal section of another modification of the tissue pneumatic separator illustrated in FIG. 10.

The further modified tissue pneumatic separator 420 shown in FIG. 19 includes an outlet connection 422 to the umbilical cord 424 through which blood or other fluids about tissue being separated may be evacuated from the area of the tissue being separated through the tissue pneumatic separator modification 420.

Thus, the umbilical cord 424 is connected directly to the passage 426 in the manifold subassembly 428 with the plug 194 removed and the passage 434 returned by a passage portion 436 whereby the fluid medium such as nitrogen gas or the like flows through the passage 430 to the left as shown in FIG. 19 (reverse venturi effect).

Figure 13:
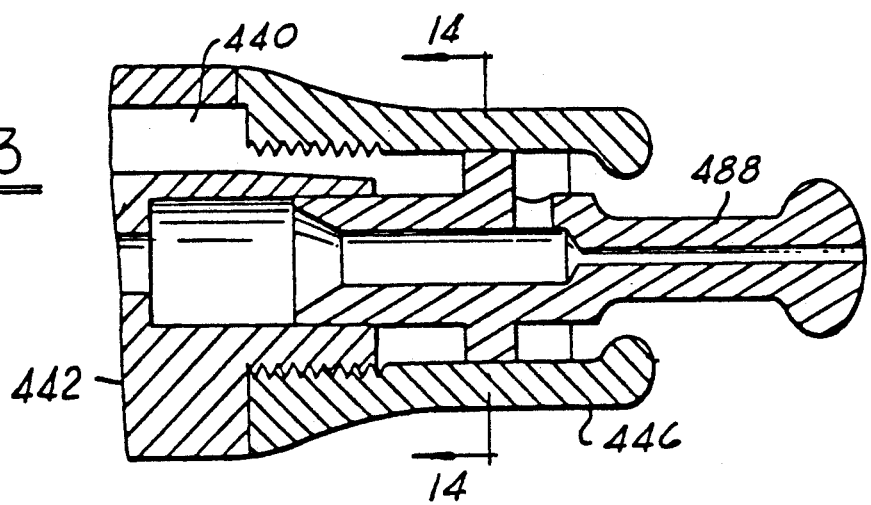
FIG. 13 is a longitudinal section view similar to FIG. 11, but showing a modified floating tip and tip retainer.

The flow of the nitrogen gas through the passage 430 to the left in FIG. 19 creates a vacuum or suction about the tip 438 as shown in FIG. 13, whereby blood and other debris from separating tissue may be sucked through passage 440 in the stem 442 to be discharged ultimately from the umbilical cord 424.

The joining ends of the passages 434 and 436 in the valve unit 432 are plugged by means of plug 444 for construction purposes.

Figure 14:
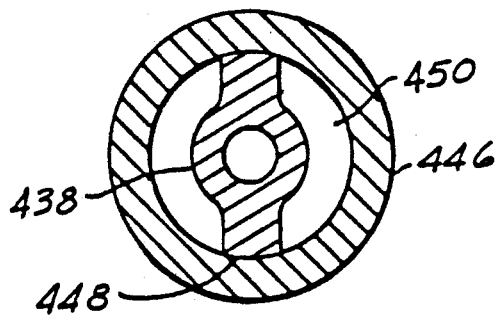
FIG. 14 is a cross section of the modified floating tip and tip retainer illustrated in FIG. 13, taken substantially on the line 14—14 in FIG. 13.

As shown best in FIG. 14, the floating tip 438 is somewhat modified as is the inside configuration of tip retainer 446. Thus, the annular flange 473 of the tip 370 is reduced to flange portions such as portions 448 shown in FIG. 14 necessary to guide the tip 438 in its reciprocal movement in the tip retainer 446. This provides enlarged areas 450 through which debris from separating tissue may be drawn into the tissue pneumatic separator 420. The enlarged openings 450 do away with the need for the slots 452 as shown in FIGS. 11 and 12.

In all other respects, the structures of and the method of operation of the tissue pneumatic separator 380 and 420 are identical with the structure and operation of the tissue pneumatic separator 120.

While different embodiments and modifications of the invention have been considered in detail above, it will be understood that other embodiments and modifications thereof are contemplated by the inventor.

Thus, according to the invention a simplifed apparatus based upon elements previously described may be used to cleanse teeth, tongue, gums and between teeth. Fluid projecting from a floating tip orifice is chosen for the cleansing purpose and contains additives abraded from a special soap-like cartridge with large surface to fluid interacting surfaces.

As shown in FIG. 20, simplified dental apparatus 460 includes the floating tip 462 which is similar to FIGS. 4 and 5, and the stem 464 of the unit features a single central duct 466 connected to a cylindrical chamber 468 closed with a threaded end cap 474 and sealed with annular seals 470 and 472. The cap 474 is connected to a small tube 476 stretched over a corrugated hollow tip 478. The tube 476 is attached at its other end to another corrugated hollow tip 480 on an annular, externally-threaded connector 482. The connector 482 is as shown in FIG. 20 threadly secured to a conventional, hot and cold water mixing, bathroom faucet 484. A special cake of dental soap may be introduced into the chamber 468 by removing the end cap 474. According to the invention, the cake of soap 486 has a cross-section of suitable configuration to provide multiple surfaces 488, 490, etc., subjected to the flow of water coming from the liquid faucet adjusted to obtain desirable temperature and liquid pressure. As the water flows over the exposed surfaces 488, 490, etc., of the soap cake 486, dissolution of soap material occurs and one or more of the following desirable effects are obtained as the operator rides the floating tip over teeth, gums and tongue without injury. These effects are cleaning, tooth enamel polishing, antisepsis, flavoring, astringent application, antifungal and bacteriacial treatment. For these purposes, the special cake of soap may include separately or in combination specific mixes of the necessary ingredients.

The method of the invention further allows a more thorough cleansing of watches and industrial machines. It may also be used for veterinary and podiatric procedures and in anatomic dissection laboratories.

Also, for example, the structure of the invention may be used as an external ear cleaning device for wax removal with the nitrogen gas being replaced by antiseptic warm oil or other suitable liquid. In such applications, the floating tip would be less likely to injure an eardrum or other sensitive portions of the external ear than would the usual cotton swabs and the like utilized currently in cleaning ear passages.

Similarly, the method used with the device which is the subject of this invention may be applied with little or no modification to the cleaning treatment or simple hygiene of other anatomical orifices.

Also, the use of the device of the invention can be counted on as an adjunct method to other surgical methods used in a plurality of different applications such as in performing an endoscopy, a brochoscopy, a proctoscopy, sigmoidoscopy, or an arthroscopy. Particularly in the case of arthroscopy, this invention would allow separation and removal of interarticular debris encountered in diagnosis and treatment of a damaged joint.

Many such procedures would, of course, require the floating protective travel of the tip to be increased and the stem to be elongated and/or the tip to be made of suitable compliant malleable material, and the device of the invention included in such procedures could include known specific viewing or illuminating structures therein.

It is the intention to include all embodiments and modifications of the new surgical method and structure of the invention defined by the appended claims within the scope of the invention.

I claim:

1. A method of use of a tissue separator having a tip which floats relative to the rest of the tissue separator comprising the step of directing a fluid medium under pressure from the tissue separator at the tissue while floating the tip of the tissue separator relative to the rest of the tissue separator on the fluid medium.

2. The method as set forth in claim 1 wherein the fluid medium is directed at the tissue along a natural cleavage plane in the tissue to separate the tissue along the natural cleavage plane.

3. The method as set forth in claim 2 and further including mechanically nudging the tissue to be separated along the natural cleavage plane with the floating tip.

4. The method as set forth in claim 2 and further including directing a moisturizing aerosol onto the tissue in the area in which the tissue is to be or is being separated.

5. The method as set forth in claim 4 wherein the moisturizing aerosol is passed through the floating tip.

6. The method as set forth in claim 4 wherein the moisturizing aerosol is passed around the floating tip.

7. The method as set forth in claim 4 wherein the moisturizing aerosol is both passed through the floating tip and passed around the floating tip.

8. The method as set forth in claim 2 and further including suctioning at least one of organic material blood, serum and other debris from the area of the tissue to be or being separated.

9. The method as set forth in claim 1 wherein the tissue is living tissue.

10. The method as set forth in claim 1 wherein the fluid medium is a gas.

11. The method as set forth in claim 1 wherein the fluid medium is a liquid.

12. The method as set forth in claim 1 and further including variably regulating the pressure on the fluid medium.

13. The method as set forth in claim 1 and further including forming pulses with the fluid medium.

14. The method as set forth in claim 1 wherein the fluid medium is passed through the floating tip.

15. The method as set forth in claim 1 wherein the fluid medium is passed around the floating tip.

16. The method as set forth in claim 1 wherein the fluid medium is both passed through the floating tip and passed around the floating tip.

17. The method as set forth in claim 16 wherein the fluid medium is alternately passed through and around the floating tip.

18. The method as set forth in claim 16 wherein the fluid medium is simultaneously passed through and around and floating tip.

19. The method as set forth in claim 1 wherein the pressurized fluid medium is water under pressure.

20. The method as set forth in claim 19 and further including obtaining the water from a fluoridated municipal water supply through a faucet.

21. The method as set forth in claim 19 and further including obtaining the water from a pressurized container.

22. The method as set forth in claim 19 and further including variably regulating the water pressure.

23. The method as set forth in claim 19 and further including forming pulses with the water.

24. The method as set forth in claim 19 wherein the tissue separator includes a body portion and including the step of passing the fluid medium over a high surface to fluid interacting soap-like, replaceable cartridge made of at least one of an abrading, cleansing, polishing and geriocidal material within the body portion prior to directing the water thus altered at the tissue.

* * * * *